United States Patent
Tsonton et al.

(10) Patent No.: US 9,345,456 B2
(45) Date of Patent: May 24, 2016

(54) BIOPSY DEVICE

(75) Inventors: Mark Tsonton, Loveland, OH (US);
Eric Thompson, Pleasant Plain, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1481 days.

(21) Appl. No.: 10/808,078

(22) Filed: Mar. 24, 2004

(65) Prior Publication Data

US 2005/0215922 A1   Sep. 29, 2005

(51) Int. Cl.
| A61B 10/02 | (2006.01) |
| A61B 17/06 | (2006.01) |
| A61B 17/00 | (2006.01) |
| A61B 19/00 | (2006.01) |
| G01R 33/28 | (2006.01) |

(52) U.S. Cl.
CPC ............. *A61B 10/0275* (2013.01); *A61B 17/06* (2013.01); *A61B 2017/00911* (2013.01); *A61B 2019/5454* (2013.01); *G01R 33/285* (2013.01)

(58) Field of Classification Search
CPC ............... A61B 10/0275; A61B 17/06; A61B 2019/5454; A61B 2017/00911; G01R 33/285
USPC .......... 600/564–567, 410, 411, 568; 606/167, 606/170, 185, 182
See application file for complete search history.

(56) References Cited

U.S. PATENT DOCUMENTS

| 5,127,419 | A | * | 7/1992 | Kaldany ........................ 600/567 |
| 5,526,822 | A | | 6/1996 | Burbank et al. |
| 5,607,401 | A | * | 3/1997 | Humphrey .................... 604/239 |
| 5,738,632 | A | * | 4/1998 | Karasawa ..................... 600/410 |
| 5,895,401 | A | | 4/1999 | Daum et al. |
| 5,944,673 | A | * | 8/1999 | Gregoire et al. .............. 600/564 |
| 6,017,356 | A | * | 1/2000 | Frederick et al. ............. 606/185 |
| 6,086,544 | A | | 7/2000 | Hibner et al. |
| 6,258,071 | B1 | | 7/2001 | Brookes |
| 6,620,111 | B2 | | 9/2003 | Stephens et al. |
| 6,626,849 | B2 | * | 9/2003 | Huitema et al. .............. 600/564 |
| 6,638,235 | B2 | | 10/2003 | Miller et al. |
| 6,758,824 | B1 | * | 7/2004 | Miller et al. ................... 600/568 |
| 7,236,816 | B2 | * | 6/2007 | Kumar et al. .................. 600/411 |
| 7,725,161 | B2 | * | 5/2010 | Karmarkar et al. ........... 600/423 |
| 2002/0026201 | A1 | * | 2/2002 | Foerster et al. ............... 606/116 |
| 2003/0028094 | A1 | * | 2/2003 | Kumar et al. .................. 600/410 |
| 2003/0032895 | A1 | | 2/2003 | Fisher |
| 2003/0109801 | A1 | * | 6/2003 | Rhad et al. .................... 600/564 |
| 2003/0109803 | A1 | | 6/2003 | Huitema et al. |

(Continued)

FOREIGN PATENT DOCUMENTS

| AU | 2005200972 | 10/2005 |
| CN | 1676105 A | 10/2005 |

(Continued)

OTHER PUBLICATIONS

EPO Search Report dated Jul. 11, 2005 for corresponding patent application, European Patent Application No. EP05251797.

*Primary Examiner* — Sean Doughtery
(74) *Attorney, Agent, or Firm* — Frost Brown Todd LLC

(57) ABSTRACT

An improved needle assembly is provided. A distal portion of the needle can be formed of a first material which does not interfere with MRI imaging of a tissue receiving port disposed in the distal needle portion. A proximal needle portion can be formed of a second, different material. The proximal needle portion can provide strength and stiffness.

18 Claims, 11 Drawing Sheets

(56) References Cited

U.S. PATENT DOCUMENTS

| | | |
|---|---|---|
| 2003/0135148 A1 | 7/2003 | Dextradeur et al. |
| 2003/0199753 A1 | 10/2003 | Hibner et al. |
| 2003/0199754 A1 | 10/2003 | Hibner et al. |
| 2003/0199785 A1 | 10/2003 | Hibner et al. |
| 2003/0203140 A1* | 10/2003 | Sapatova et al. ............. 428/35.7 |
| 2004/0143197 A1* | 7/2004 | Soukup et al. ................ 600/585 |
| 2005/0215922 A1 | 9/2005 | Tsonton et al. |

FOREIGN PATENT DOCUMENTS

| | | |
|---|---|---|
| EP | 1232766 A2 | 8/2002 |
| EP | 5251796 | 7/2005 |
| EP | 1579810 | 9/2005 |
| JP | 49597731 B2 | 12/2010 |

* cited by examiner

BIOPSY DEVICE

This applications cross references and incorporates by reference the following application filed on even date herewith: "Method of Forming a Biopsy Device" in the names of Tsonton et al, Ser. No. 10/808,077.

FIELD OF THE INVENTION

The present invention is related generally to biopsy devices, and more particularly, to an improved biopsy device for acquiring a tissue sample.

BACKGROUND OF THE INVENTION

The diagnosis and treatment of patients with cancerous tumors, pre-malignant conditions, and other disorders has long been an area of intense investigation. Non-invasive methods for examining tissue include palpation, thermography, PET, SPECT, Nuclear imaging, X-ray, MRI, CT, and ultrasound imaging. When the physician suspects that tissue may contain cancerous cells, a biopsy may be done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. For a percutaneous biopsy, a needle-like instrument is used through a very small incision to access the tissue mass of interest and to obtain a tissue sample for later examination and analysis.

The advantages of the percutaneous method as compared to the open method are significant: less recovery time for the patient, less pain, less surgical time, lower cost, less risk of injury to adjacent bodily tissues such as nerves, and less disfigurement of the patient's anatomy. Use of the percutaneous method in combination with artificial imaging devices such as X-ray and ultrasound has resulted in highly reliable diagnoses and treatments.

Generally there are two ways to percutaneously obtain a portion of tissue from within the body, by aspiration or by core sampling. Aspiration of the tissue through a fine needle requires the tissue to be fragmented into small enough pieces to be withdrawn in a fluid medium. The method is less intrusive than other known sampling techniques, but one can only examine cells in the liquid (cytology) and not the cells and the structure (pathology). In core sampling, a core or fragment of tissue is obtained for histologic examination, genetic tests, which may be done via a frozen or paraffin section. The type of biopsy used depends mainly on various factors present in the patient, and no single procedure is ideal for all cases. However, core biopsies seem to be more widely used by physicians.

The following patent documents are incorporated herein by reference for the purpose of illustrating biopsy devices and methods: U.S. Pat. No. 5,526,822 issued Jun. 18, 1996; U.S. Pat. No. 5,895,401 issued Apr. 20, 1999; U.S. Pat. No. 6,086,544 issued Jul. 11, 2000; U.S. Pat. No. 6,620,111 issued Sep. 16, 2003; U.S. Pat. No. 6,626,849 issued Sep. 30, 2003; U.S. Pat. No. 6,638,235 issued Oct. 28, 2003; US Patent Application 2003/0109803 published Jun. 12, 2003; US Patent Application 2003/0199753 published Oct. 23, 2003; US Patent Application 2003/0199754 published Oct. 23, 2003; US Patent Application 2003/0199785 published Oct. 23, 2003; and U.S. Ser. No. 08/825,899 filed on Apr. 2, 1997.

In making and using biopsy devices for use with magnetic resonance imaging (MRI) machines, it is desirable to avoid distortion of the image provided by the MRI machine, yet still be able to accurately position the needle with respect to a desired location in a tissue mass.

SUMMARY OF THE INVENTION

The present invention recognizes the desirability of providing a biopsy device, which is compatible for use with MRI devices, while maintaining strength and stiffness characteristics of a biopsy device, which are useful in providing for accurate placement of a biopsy needle at a target tissue site. The present invention also recognizes the desirability of providing a method for making an MRI compatible biopsy device while maintaining the strength, stiffness, and/or other advantageous characteristics of the biopsy device.

In one embodiment, the present invention provides a biopsy device suitable for use with an MRI device. The biopsy device includes a needle having a proximal segment and a distal segment. The distal needle segment includes a tissue receiving port, and the distal needle segment is formed of a first material, which does not interfere with MRI imaging of the portion of the needle associated with the tissue receiving port, such as the edges of the tissue receiving port. The proximal needle segment is formed at least of a second material different from the first material. The second material can be selected such that the proximal needle segment provides the needle with strength and/or stiffness suitable to provide accurate placement of the tissue receiving port of the needle, with respect to a tissue mass to be sampled.

In one embodiment, the first material can be non-metallic and non-magnetic, and the second material can be a non-magnetic metal. The second material can be spaced at least about 0.5 inch from a proximal edge of the tissue receiving port.

The needle can further comprise a distal piercing tip. The distal piercing tip can be formed of a material which does not interfere with MRI imaging of the portion of the probe body associated with the tissue receiving port, such as the edges of the tissue receiving port. The distal piercing tip can be formed of a non-metallic material, such as a ceramic or glass material.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

FIGS. 1-6 illustrate a biopsy device according to U.S. Pat. No. 6,626,849. FIGS. 7-12 illustrate embodiments of a biopsy device and a mold for making a biopsy device according to the present invention.

Figure 1:
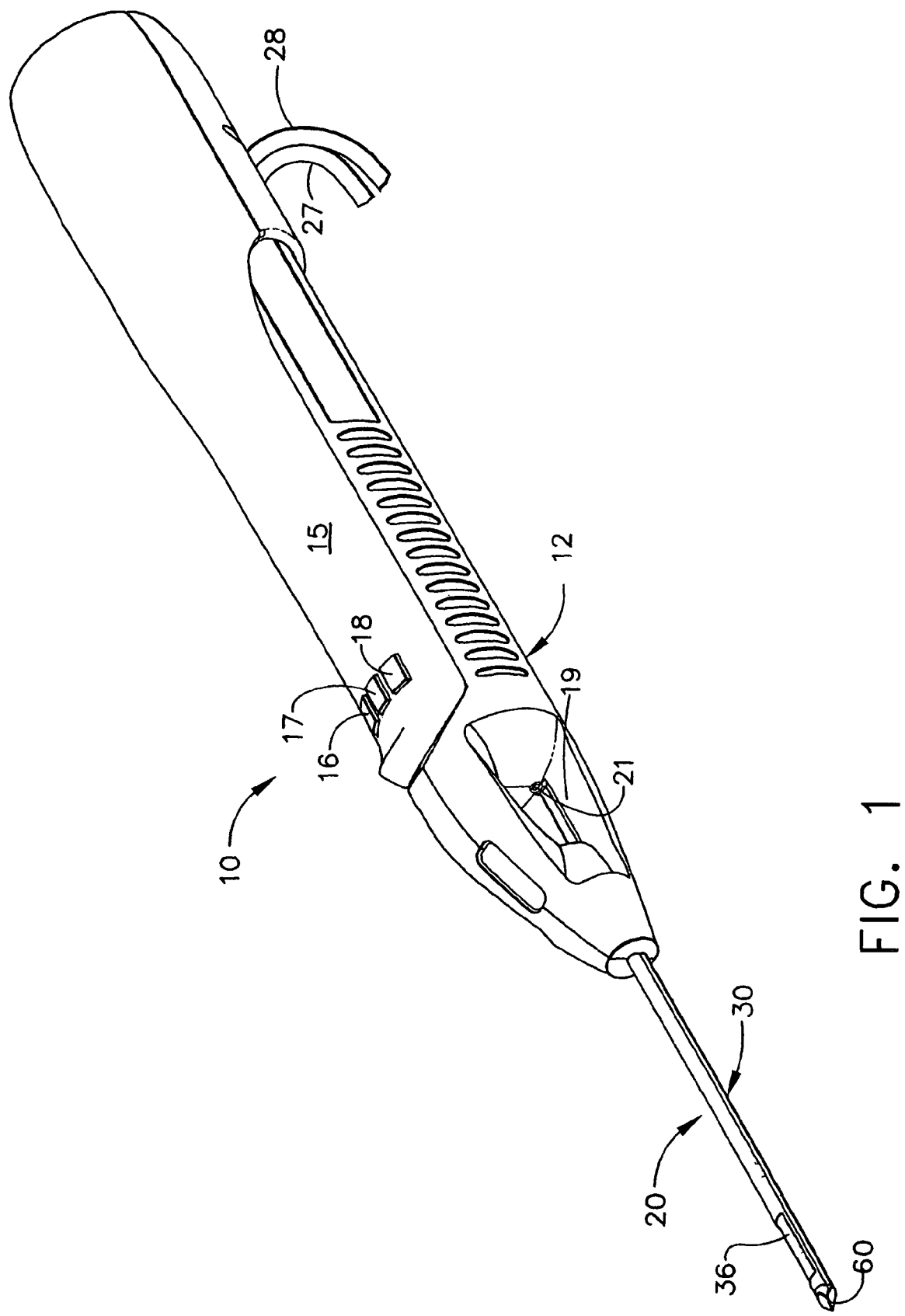
FIG. 1 is an isometric view of a hand held vacuum assisted biopsy device constructed in accordance with U.S. Pat. No. 6,628,849.

FIG. 1 shows a hand-held vacuum assisted biopsy device 10 comprising a needle assembly 20 and a holster 15, as described in U.S. Pat. No. 6,626,849. Needle assembly 20 is detachably connected to holster 15. Together they constitute a lightweight, ergonomically shaped, hand manipulatable portion referred to as handpiece 12. Since handpiece 12 is manipulated by the operator's hand rather than by an electromechanical arm, the operator may steer the handpiece 12 with great freedom towards the tissue mass of interest. The surgeon has tactile feedback while doing so and can thus, ascertain to a significant degree, the density and hardness of tissue being encountered. In addition, handpiece 12 may be held approximately parallel to the chest wall of a patient for obtaining tissue portions closer to the chest wall than may be obtained when using an instrument mounted to an electromechanical arm.

The device includes a means for obtaining a tissue sample. Holster 15 includes a forward button 16 which may be used to move cutter 21 (shown in FIG. 1) distally though cutter lumen 32 and sever tissue collected in port 36. Holster 15 further includes a reverse button 17 which may be used to move cutter 21 proximally through cutter lumen 32 and thereby moving the tissue sample in port 36 to a tissue collection surface 19. A vacuum button 18 on holster 15 is used to open or close first and second vacuum lines, 27 and 28, for activating a vacuum lumen 34 so as to cause tissue to become disposed within port 36.

Figure 2:
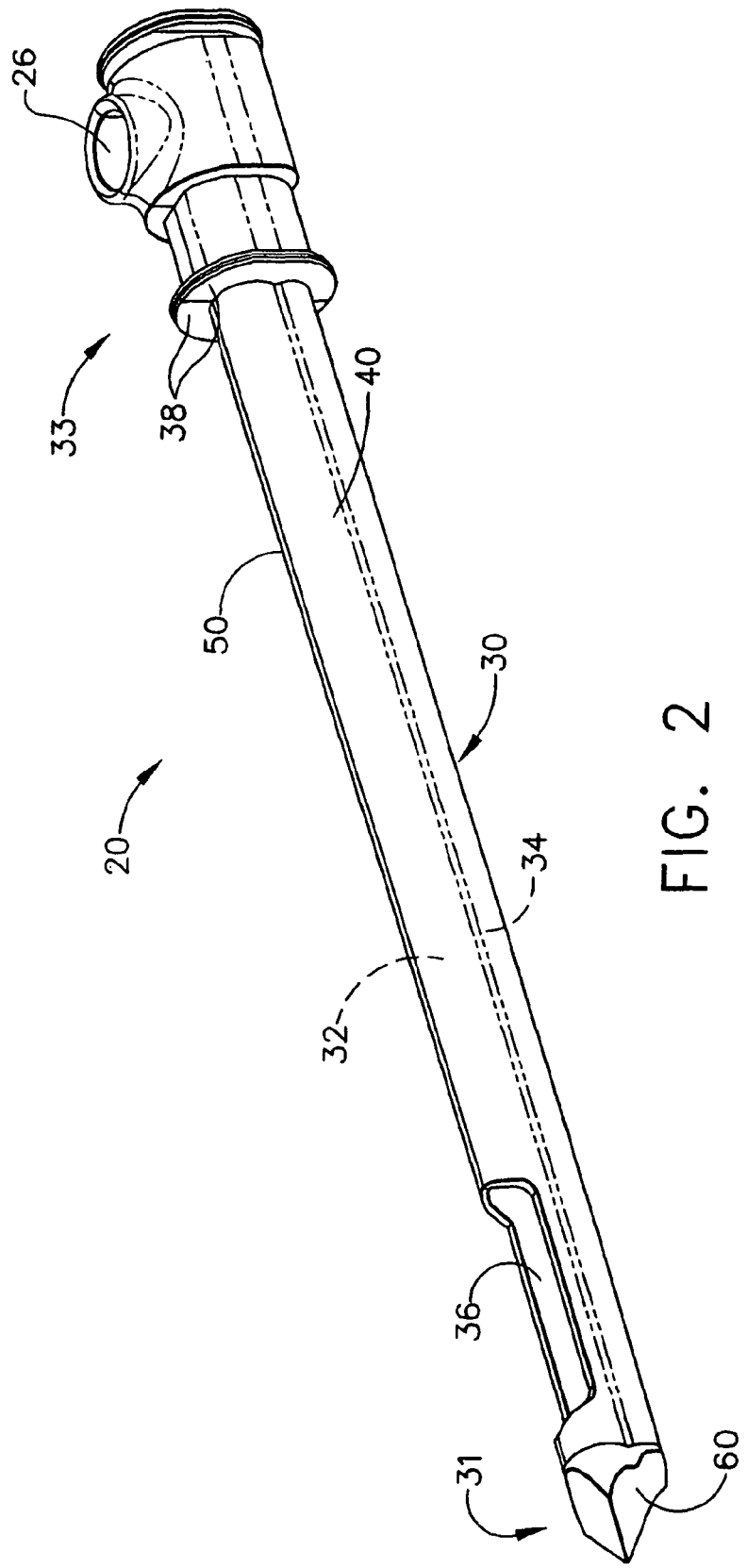
FIG. 2 is an isometric view of the elongated needle of the hand held vacuum assisted biopsy device of FIG. 1.

Referring now to FIG. 2 there is shown an isometric view of the needle assembly 20 of the hand held vacuum assisted biopsy device 10 of FIG. 1. Needle assembly 20 includes an elongated needle 30 having a distal end 31, a proximal end 33 and a longitudinal axis therebetween. Needle assembly 20 has a needle tip 60 at its distal end for penetrating the soft tissue of a surgical patient. Elongated needle 30 comprises a cutter lumen 32 and a vacuum chamber lumen 34.

At the distal end of the elongated needle 30 is a needle tip 60, which is sharpened and is preferably made from an MRI compatible resin such as Ultem or Vectra. Needle tip 60 is designed to penetrate soft tissue, such as the breast of a female surgical patient. In this embodiment, needle tip 60 is a three-sided pyramidal shaped point, although the needle tip 60 configuration may also have other shapes.

Figure 3:
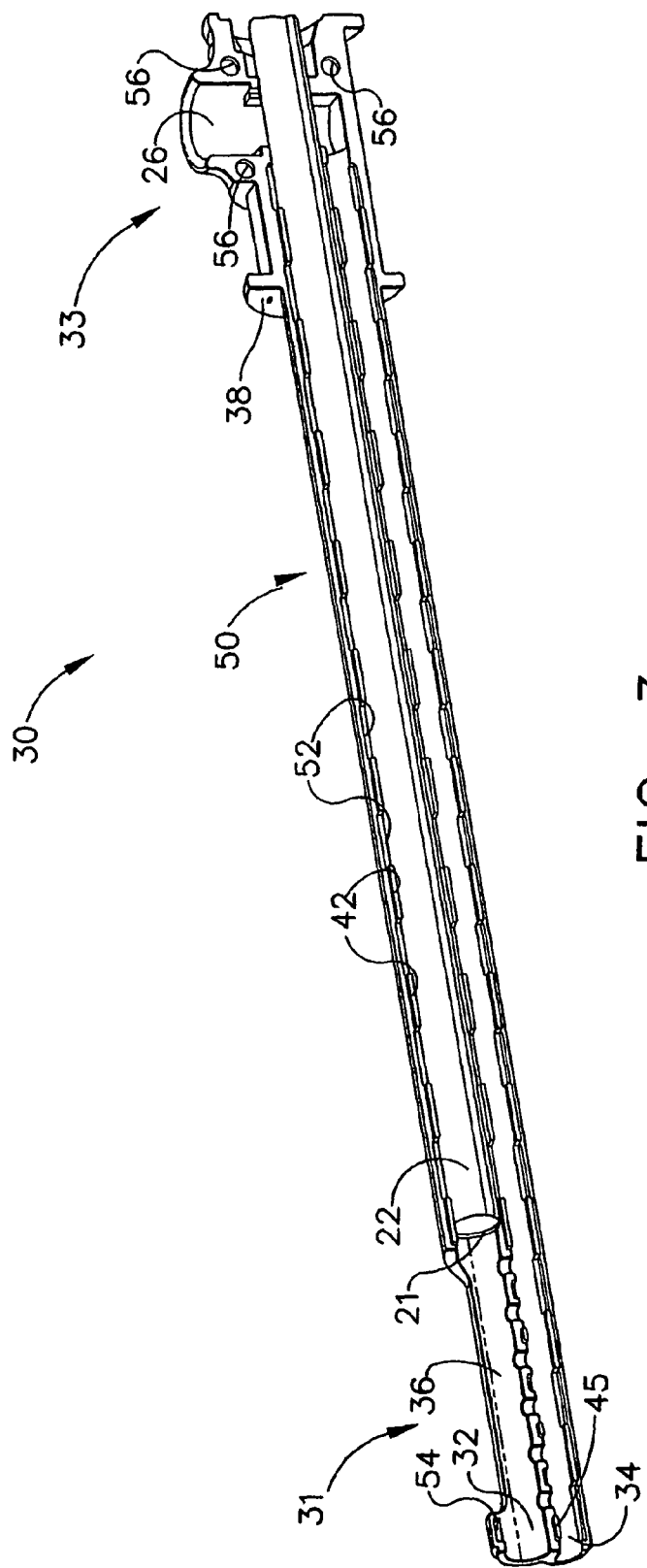
FIG. 3 is an isometric view of the right body member of the elongated needle of the hand held vacuum assisted biopsy device of FIG. 1. A cutter tube liner is illustrated in assembly with the elongated needle.

Referring now to FIG. 3, elongated needle 30 can be made from a thermoplastic material such as Vectra A130 or B130 liquid crystal polymer, although other MRI compatible resins may be available from Ticona of Summit, N.J. Elongated needle 30 includes a cutter lumen 32 which houses the cutter 21 (shown in FIG. 1). Adjacent the distal end 31 of the cutter lumen 32 is a port 36 for receiving the tissue that is extracted from a surgical patient by the cutter 21. Joined alongside the cutter lumen 32 is a vacuum chamber lumen 34. The vacuum chamber lumen 34 receives vacuum from the second vacuum line 28 which is connected the vacuum chamber lumen 34 on the elongated needle 30 by the vacuum manifold 26 which is located at the proximal end 33 of elongated needle 30. Also located at the proximal end of the elongated needle 30 is a flange 38, which allows the elongated needle 30 and needle assembly 20 to interlock with the handpiece 12 on the handheld vacuum assisted biopsy device 10. The liner 22, discussed below, can be made from a MRI compatible material, such as a polypropylene such as Prolene available from Ethicon, Inc., Somerville N.J., or a material known as Radel-5000, available from British Petroleum, London UK.

Figure 4:
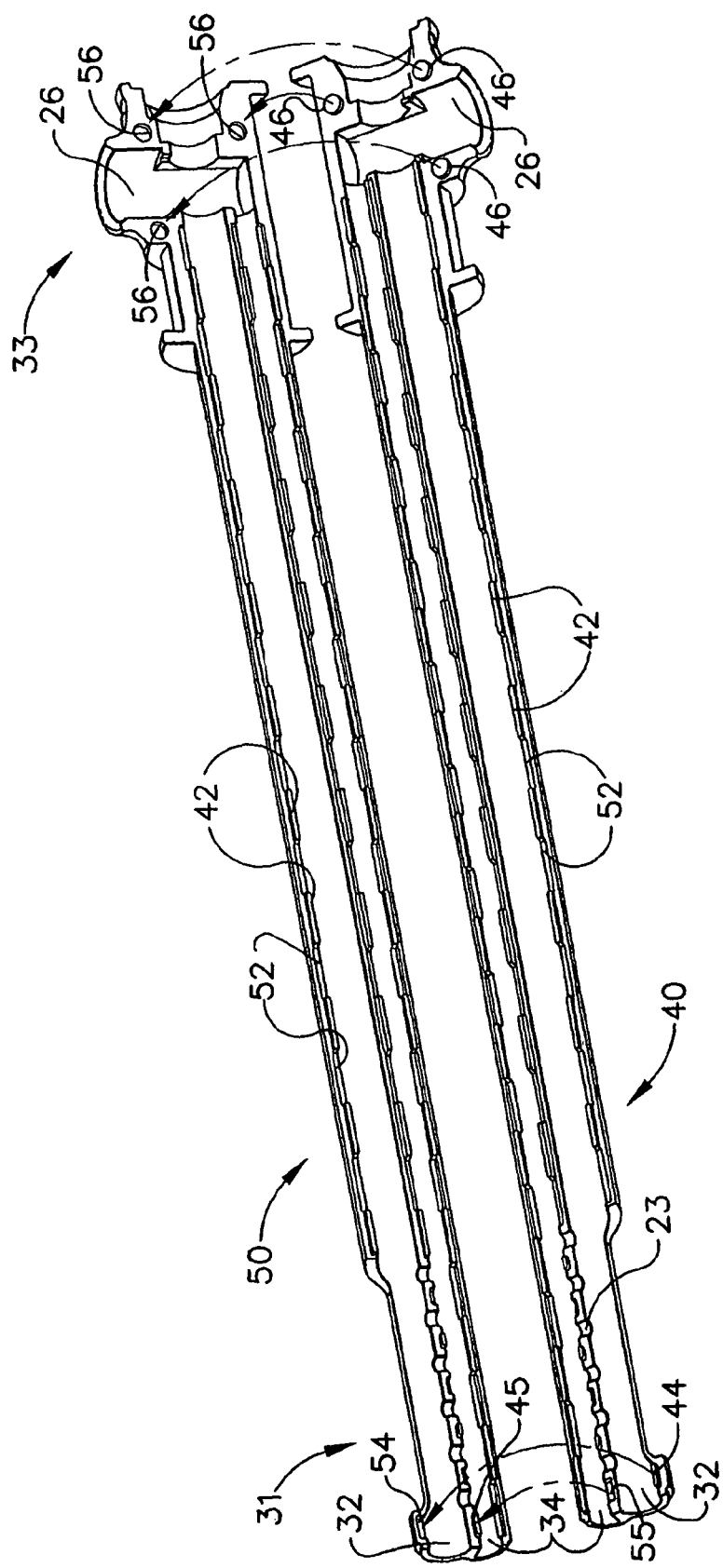
FIG. 4 is an exploded isometric view of the separated left body member and right body member of the elongated needle of the hand held vacuum assisted biopsy device of FIG. 1.

Referring to FIG. 4, the needle 30 of FIGS. 1-4 can be formed from a left body member 40 and a right body member 50 on either side of the longitudinal axis. The edges of the halves 40 and 50 are gated for easy part filling, and the edges are stepped with ridges that allow the two halves 40 and 50 to attach together with ease. Preferably needle 30 is molded from a thermoplastic, such as Vectra A130 or Vectra B130 liquid crystal polymer. Other glass fiber reinforced resins known to those skilled in the art could also be used. Preferably the probe is made from a polymer material having the combination of high stiffness, low viscosity, and low mold shrink rate, such as LCP resins.

During assembly of the elongated needle 30, the left body member 40 and right body member 50 of the elongated needle 30 can be pushed together. Once the left body member 40 and the right body member 50 are pressed together, a thin-walled sleeve of high strength tubing is slipped over the elongated needle and is shrink fitted into place. The shrink tubing holds the left body member 40 and the right body member 50 together for easier handling prior to adhesive curing. In addition, the shrink tubing makes the exterior of the elongated needle 30 smoother for reduced insertion forces.

Referring back to FIG. 3, there is shown the right body member 50 of the elongated needle 30, separated from the left body member 40, which has been omitted from this figure for clarity. The right body member 50 has upper and lower ends comprising alternating male and female portions or members, 42 and 52, which alternate and are arranged axially along the length of the right body member 50 of the elongated needle 30. In addition to the male and female members, 42 and 52, there is an upper female distal member 54 and a lower male distal member 45, both of which are located at he distal end of the right body member 50. The upper female distal member 54 is located just below the distal end of the cutter lumen 32 and above the distal end of the vacuum chamber lumen 34. At the proximal end of the right body member 50 are three female receivers 56 which surround the vacuum manifold 26 at the proximal end of the right body member 50.

Still referring to FIG. 3, needle 20 includes a cutter tube liner 22, which helps keep adhesive out of the lumen to provide a smooth surface thereon. Liner 22 generally abuts in the inner surface of cutter 20 along lumen 32. The distal end 31 of liner 22 is proximal to port 36 but otherwise is disposed along the length of lumen 32. The cutter tube liner 22 is formed from a thin-walled extrusion of a low-friction, abrasion-resistant plastic, such as polypropylene, polyetherimide or polyethersulfone. The cutter tube liner 22 provides a smooth, low-friction, abrasion-resistant surface for the cutter 21.

Referring again to FIG. 4 there is shown an exploded isometric view of the elongate needle 30 of the hand held vacuum assisted biopsy device 10 of FIG. 1. Both the left body member 40 and the right body member 50 of the elongated needle 30 are shown. The male features 42 which are arranged axially on the left body member 40, mate to the female features 52 which are arrange axially on the right body member 50. The male features 42 arranged axially on the right body member 50 mates to the female features 52 which are arranged axially on the left body member 40.

In addition to male and female members, 42 and 52, which are arranged axially and mate, the left body half 40 and right body member 50 have additional features that mate at both the proximal and the distal ends. At the proximal end of the right body member 50 are three female receivers 56 which surround the vacuum manifold 26. At the proximal end of the left body member 40 are three male bosses 46 which surround the vacuum manifold 36 and correspond to the three female receivers 56 on the right body member 50. When the left body member 40 and the right body member 50 are pushed together, the three female receivers 56 on the proximal end of the left body member 40. The proximal end of the elongated needle 30 is thus, retained by the three female receivers 56 and three male bosses 46, which mate at the proximal end of the elongated needle 30.

The needle tip 60 at the distal end of the elongated needle 30 is retained by the upper female distal part 54 and the upper male distal portion 44 and the lower female distal portion 55 on the left body member 40. The upper male distal portion 44 is located above the cutter lumen 32 at the distal end on the left body member 40, and the lower female distal part 55 is located below the cutter lumen 32 and above the vacuum chamber lumen 34 at the distal end of the left body member 40. On the right body 50 is an upper female distal part 54 and a lower male distal portion 45, which correspond to the upper male distal portion 44 and the lower female distal part 55 on the left body member 40. The upper female distal part 54 is located above the cutter lumen 32 at the distal end of the right body member 50, and the lower male distal portion 45 is located below the cutter lumen 32 and above the vacuum chamber lumen 34 at the distal end of the right body member 50.

Still referring to FIG. 4, the right body member 50 and left body member 40 can be configured so that when the member 50 and the member 40 are joined, the combined members provide the interlumen vacuum holes 23, which are located below the tissue receiving port 36 on the distal end of the elongated needle 30. The interlumen vacuum holes 23 can be in the form of six cylindrically shaped holes which are open to port 36. Vacuum communicated from vacuum lumen 34 through holes 23 can be used to draw tissue into the cutter lumen 32. Cutter 21 can have a sharpened distal end adapted to cut tissue, and can rotationally driven as it is advanced distally past tissue port 36, thereby severing tissue drawn into cutter lumen 32. The cutter 21 can then be retracted and the severed tissue sample deposited at collection surface 19 (FIG. 1) by retracting proximally.

Still referring to FIG. 4, the male and female members, 42 and 52, which mate and are located on the left body member 40 and the right body member 50 have a number of distinct advantages. The male and female members, 42 and 52, on the left body member 40 and right body member 50 orient the left body member 40 and right body member 50 during assembly of the elongated needle 30.

The male and female members, 42 and 52, which mate, are also key factors in increasing both the strength and lateral bending stiffness of the elongated needle 30. When the needle 30 is subjected to a lateral bending moment, nearly all of the material being loaded axially is the high-strength, high stiffness body material. Only the small amount of adhesive that is used to fill the axial clearances between the male and female members, 42 and 52, which mate, is of a lower stiffness. A conventional bonded joint would result in the bond line being loaded in a manner similar to that used for adhesive peel strength testing, which is the most severe type of loading for an adhesive joint. In contrast to this, the male female members, 42 and 52, which mate, would create lateral bond surfaces along the elongated needle 30. This substantially increases the bond line length of the elongated needle 30. Because of significant portions of the bond line being loaded in shear, the strength and lateral stiffness of the elongated needle 30 is increased. This is improved over a single piece molded cylinder in that with the bond line loaded in shear, the elongated needle 30 will be able to sustain bending moments of its joints rather than at its base, which decreases the possibility of breakage.

Figure 5:
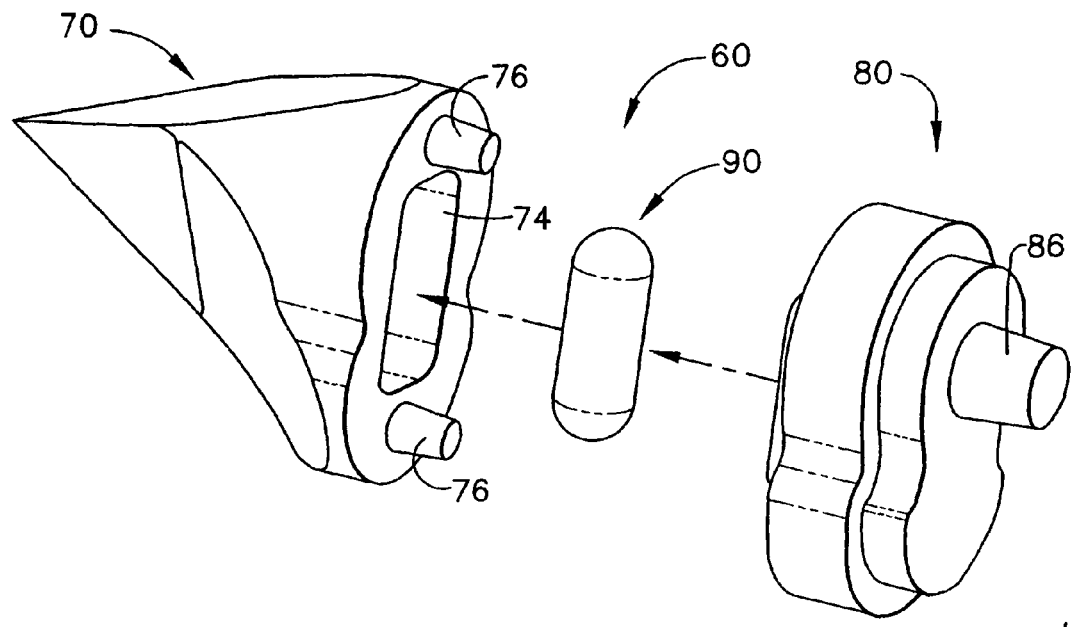
FIG. 5 is an exploded isometric view of the two member needle tip on the elongated needle of the hand held vacuum assisted biopsy device of FIG. 1 as viewed from the proximal side thereof.

FIG. 5 shows and exploded isometric view of the needle tip 60 of the elongated needle 30 of the hand held vacuum assisted biopsy device 10 of FIG. 1 as viewed from the proximal side thereof. The needle tip 60 has two halves; a composite tip member 70, and a composite hub member 80. Both the composite tip member 70 and the composite hub member 80 are preferably molded from a magnetic Resonance Imaging (MRI) compatible resin such as Ultem or Vectra ceramic or other MRI compatible materials known to those skilled in the art is sharp. The composite tip member 70 has a three-sided pyramidal shaped point, but may also have other shapes. The composite tip member 70 has a hollow cavity 74 and protruding connectors 76. The two protruding connectors 76 are inserted into the two receiving holes 82 on the composite hub member 80 when the composite hub member 80 is pushed into the composite tip member 70 during assembly. Cavity preferably contains a capsule 90 made from a material which will leave and MRI artifact. Having a capsule 90 made from and MRI artifact leaving material is necessary because since the elongated needle 30 is made of an MRI compatible resin, the elongated needle 30 does not show up on an MRI scan. Therefore, it is difficult for a physician to discern the orientation of the elongated needle 30 during and MRI scan MRI artifact leaving material 90 solves the aforementioned problems in that a needle tip 60 leaves a small, but not troublesome artifact on an MRI scan. This small, artifact indicates the orientation of the elongated needle 30 relative to the sight of biopsy, and where the tissue receiving bowl begins during and MRI scan. The MRI artifact leaving material 90 that is preferred is a capsule of Gadolinium. However, there are other materials that could be put into the hollow cavity 74 of the composite tip member 70 that would leave and acceptable MRI artifact. These include, but not limited to: liquid Gadolinium, Titanium Wire, Aluminum, Copper, Brass Iron, and Bronze.

Figure 6:
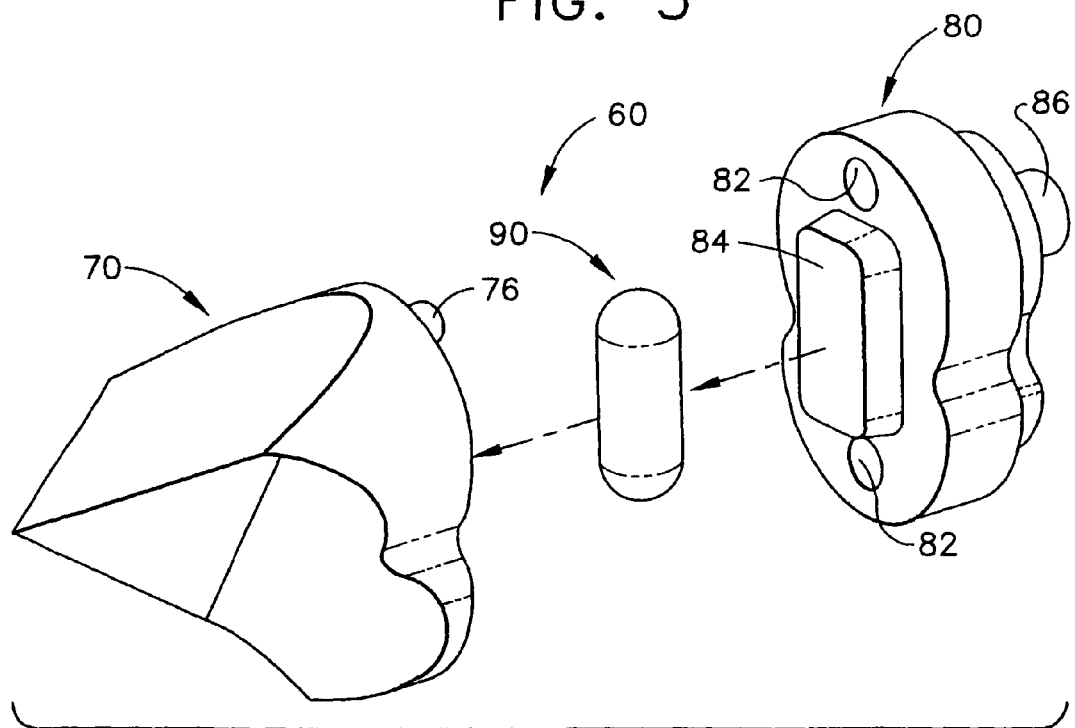
FIG. 6 is an exploded isometric view of the two member needle tip of the elongated needle of the hand held vacuum assisted biopsy device of FIG. 1 as viewed from the distal end thereof.

FIG. 6 shows an exploded isometric view of the needle tip 60 of the elongated needle 30 of the hand held vacuum assisted biopsy device 10 of FIG. 1 as viewed from the distal end thereof. This figure clearly illustrated the components on the composite hub member 80. On the distal end of the composite hub member 80 is a male part 84, which pushes the MRI artifact leaving material 80 down into the hollow cavity 74 on the composite tip member 70. Also located on the distal end of the composite hub member 80 is a knock out boss 86, which pushes a collected breast tissue sample into the end of the cutter tube 21 the hand held vacuum assisted biopsy device 10 during a breast biopsy. The two receiving holes 82 on the composite hub member 80 receive the two protruding connectors 76 on the composite tip member 70 when the composite tip member 70 and composite hub member 80 are pushed together. The reception of the two protruding connectors 76 on the composite tip member 70 by the two receiving holes 82 on the composite hub member 80 locks the composite tip member 70 and the composite hub member 80 together, and seals the MRI artifact leaving material 90 in the hollow cavity 74 in between the composite tip member 70 and composite hub member 80.

In using the hand member vacuum assisted biopsy device 10, as shown in FIG. 1, for a breast biopsy in an MRI environment, physician will first positioned outside of the MRI magnet, the patient is moved into the MRI magnet and imaging of the breast is performed. During imaging of the breast, serial slices of the breast are examined, and a contrast agent is administered to highlight suspicious areas of breast tissue. At this time, the location of the suspicious breast tissue is determined relative to the compression grid.

After the location of the suspicious breast tissue is determined, the patient is moved outside the magnet. Local anesthesia is administered to the patient and the probe 20 is inserted into the area of suspicious breast tissue.

After the probe is inserted into the suspicious area of breast tissue, the patient is moved back into the MRI magnet and a set of images of the breast are taken. The sets of images confirm that the probe 20 is adjacent to the suspicious breast tissue, the patient is moved outside of the MRI magnet and the hand held vacuum assisted biopsy device 10 of FIG. 1 is then inserted into the sleeve, replacing the obturator.

After the hand held vacuum assisted biopsy device 10 of FIG. 1 is inserted through the sleeve; multiple tissue samples are taken. In taking multiple tissue samples, the needle tip 60 as the distal end of the elongated needle 30 on the hand held vacuum assisted biopsy 10, of FIG. 1, penetrates the breast in the area that is adjacent of the suspicious breast tissue. Prior to, and during penetration by the needle tip 60, the cutter 21 is fully forward, and is advanced forward through the cutter lumen 32 by pressing the forward button 16 on the holster 15 of the vacuum assisted biopsy device 10 of FIG. 1.

Once the elongated needle 30 is positioned in the area adjacent to the suspicious breast tissue, vacuum suction is applied to he vacuum chamber lumen 34. The vacuum suction is applied by pressing the vacuum button 18 on the holster 15 of the hand held vacuum assisted biopsy device 10 of FIG. 1. Pressing the vacuum button 18 on the holster 15 opens the second vacuum line 28, which transports vacuum suction through the handpiece 12 of the hand held vacuum assisted biopsy device 10 and into the vacuum chamber lumen 34 on the elongated needle 30. The second vacuum line 28 runs through the handpiece 12 of the hand held vacuum assisted biopsy device 10 and into the elongated needle 30 through the vacuum manifold 24 at he proximal end of the elongated needle 30. The vacuum suction that is applied to the vacuum chamber lumen travels from the proximal, of the distal end of the vacuum chamber lumen 34, below the interlumen vacuum holes 23. The interlumen vacuum holes 23 receive suction from the vacuum chamber lumen 34.

The suction from the interlumen vacuum holes 23 actively pulls breast tissue through the port 36 and into the cutter lumen 32 on the elongated needle 30. After the breast tissue is pulled into the elongated needle 30 through the port 36, the cutter 21 begins to rotate and advances through the breast tissue until a sample has been obtained. After the breast tissue sample has been obtained, the elongated needle 30 is rotated to position the port 36 toward a different clockwise position in preparation for obtaining the next tissue sample. After the elongated 30 is rotated, the cutter 21 is withdrawn backwards within the cutter lumen 32 on the elongated needle 30 and the breast tissue sample is carried back to a knock-out boss 86, which pushed the collected breast tissue sample out into a tissue collection surface 19 on the handheld vacuum assisted biopsy device 10. Vacuum suction is then reapplied to the vacuum chamber lumen 34 from the second vacuum line 28, and the aforementioned process is repeated continuously until the elongated needle 30 has been rotated clockwise once around the entire clock.

After multiple breast tissue samples have been obtained from the patient, the patient is moved back into the MRI magnet. Once in the MRI magnet, a set of images of the breast are taken in order to confirm that the suspicious breast tissue has been removed. The artifact in the probe tip is a useful point of reference to confirm after the biopsy site is marked, the breast biopsy in an MRI environment is complete.

Figure 7:
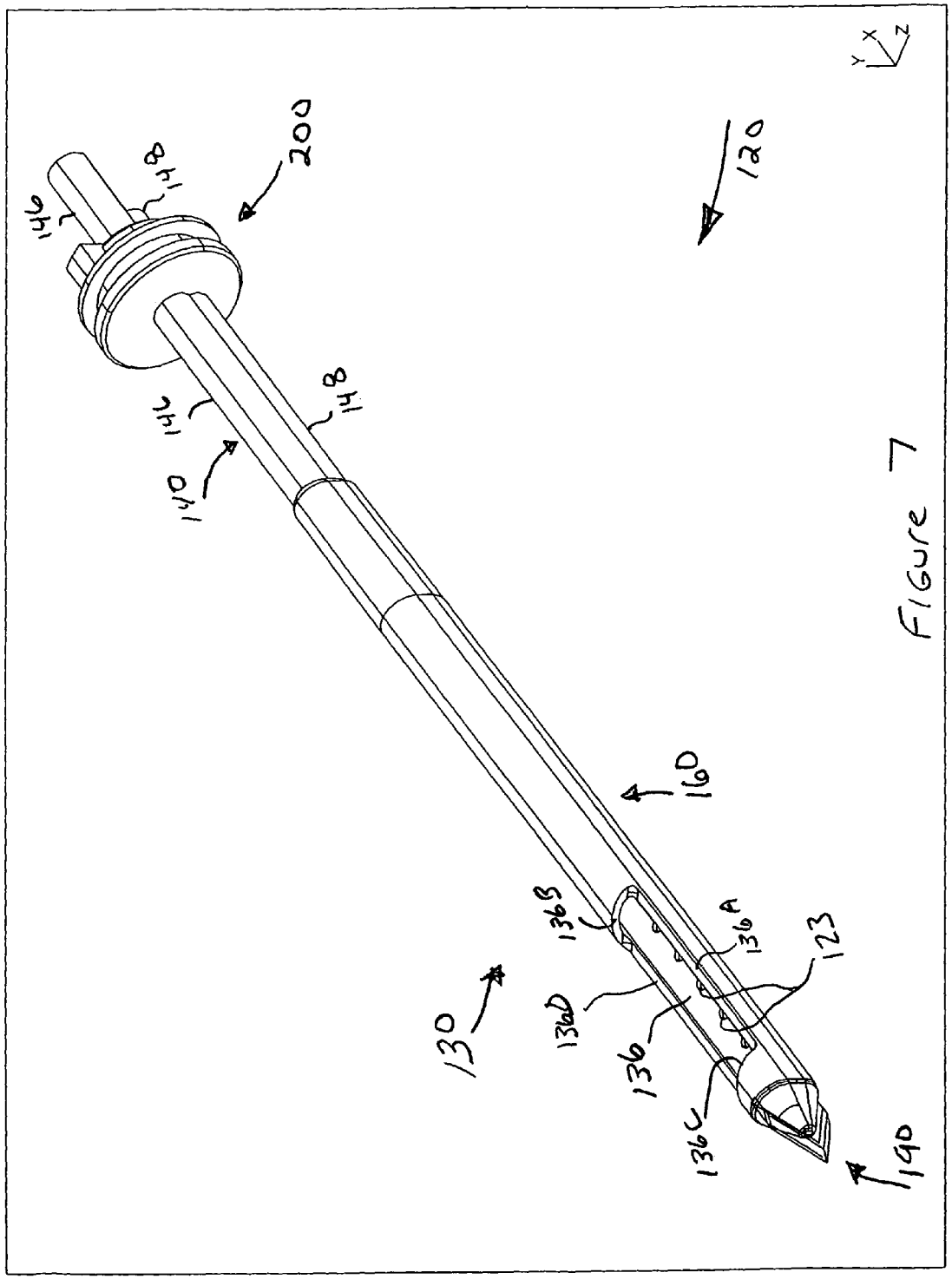
FIG. 7 is an isometric view of a biopsy device according to one embodiment of the present invention.
Figure 8:
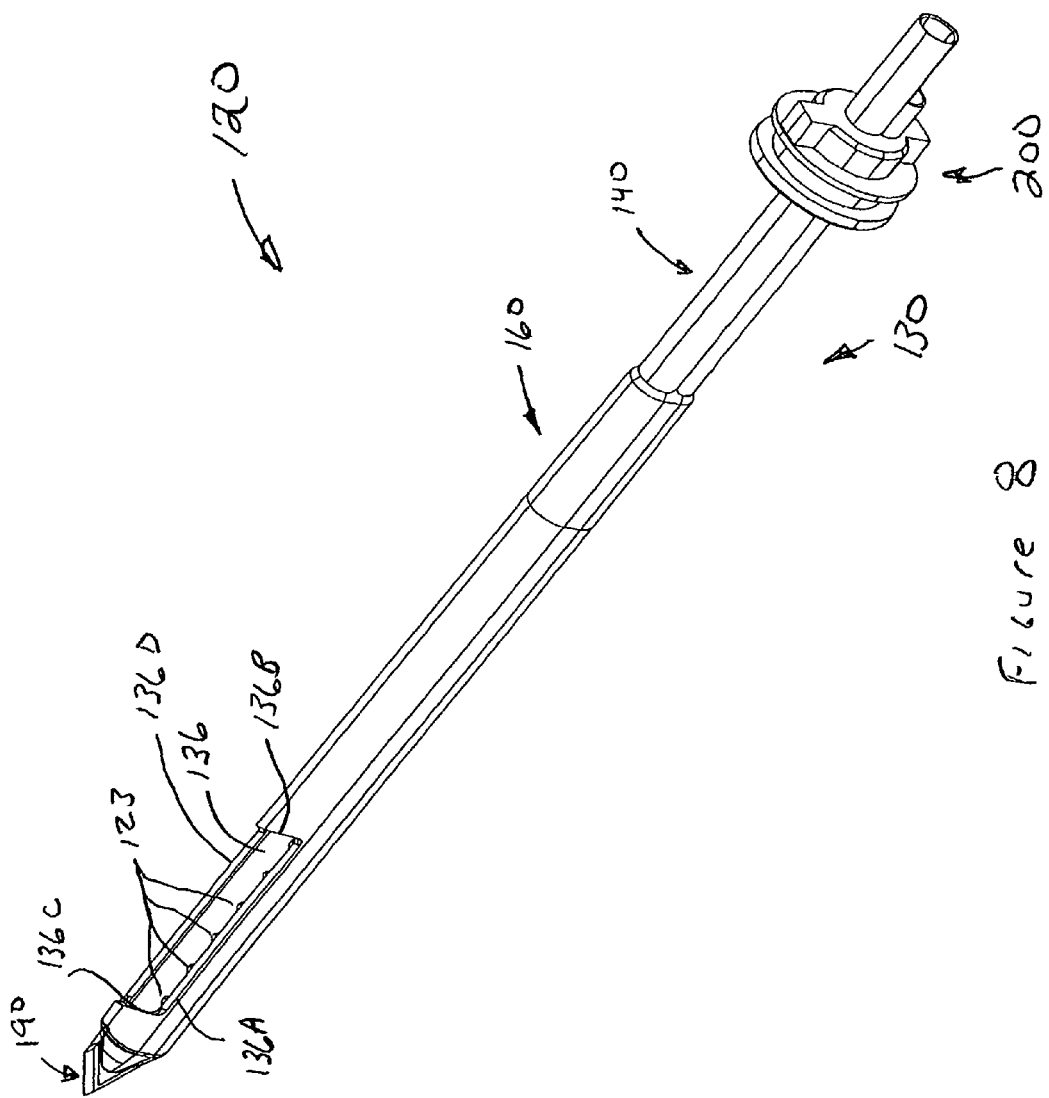
FIG. 8 is an alternate isometric view of the biopsy device of FIG. 7.
Figure 9:
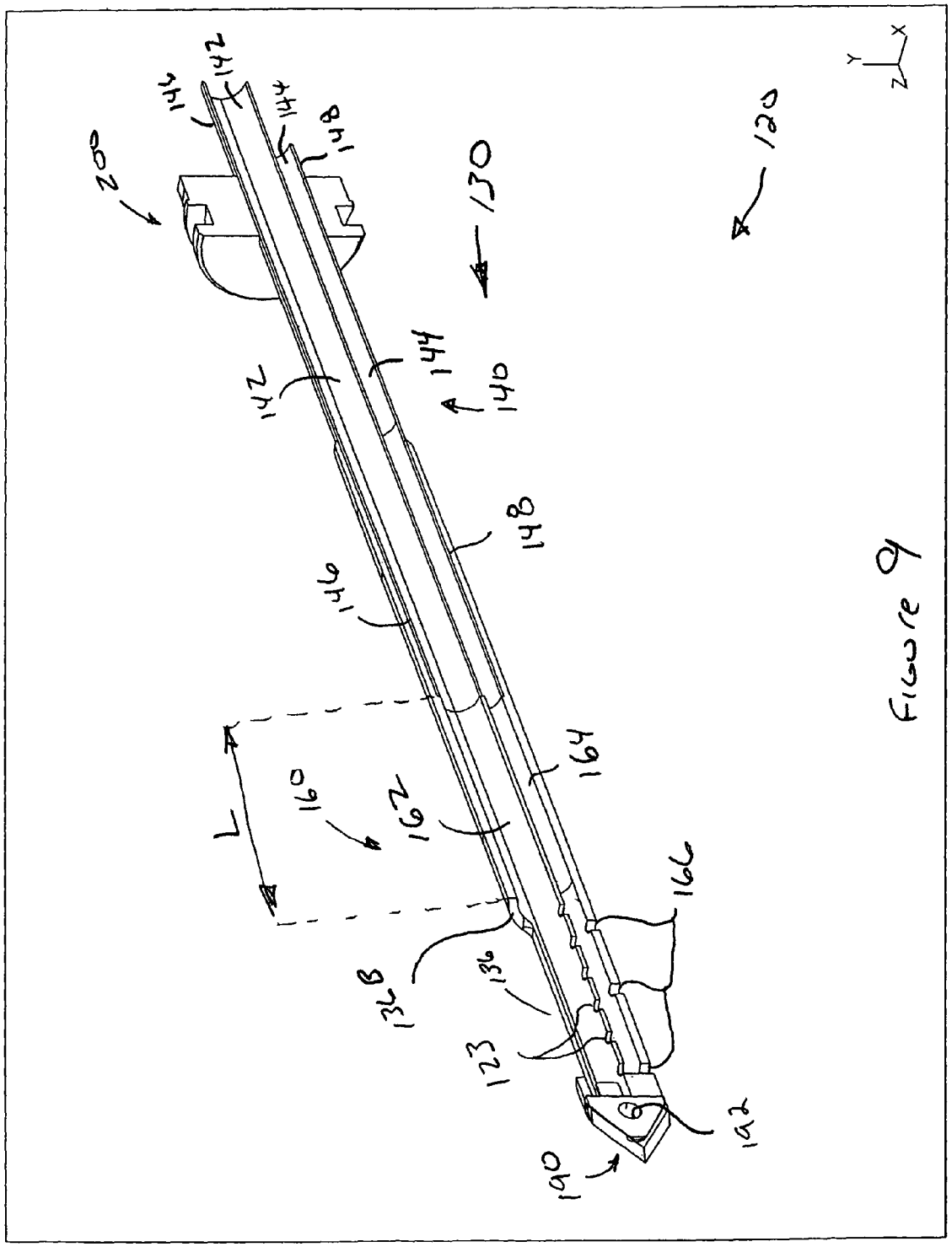
FIG. 9 is a schematic cross sectional illustration of the biopsy device of FIG. 7.

Referring now to FIGS. 7-9, an improved needle assembly 120 for use with a biopsy device is illustrated. The needle assembly 120 can be used with a handheld device such as a handpiece 12 of the type shown in FIG. 1. Alternatively, the needle assembly 120 can be used with a biopsy device which is mounted on a platform, table, or other suitable support.

Needle assembly 120 can include an elongated needle 130 and a mounting component 200. Mounting component 200 can be used to support the needle assembly 120 on a biopsy handpiece, a biopsy device base or platform, or other mounting surface for supporting a biopsy device.

The elongated needle 130 can include a distal needle segment 160 and a proximal needle segment 140. The distal needle segment 160 can comprise a tissue receiving port 136 formed therein. The distal needle segment can be formed of a first material that does not interfere with MRI imaging of a portion of the distal needle segment associated with the tissue receiving port 136. The first material can be used to form the edges 136A, B, C, and D of the port 136, and the first material can extend proximally from edge 136B and distally from edge 136C. The distal needle segment 160 can include interlumen vacuum holes 123 for use in drawing tissue into the port 136, the holes 123 illustrated in FIGS. 7, 8, and 9.

By the phrase "not interfere with MRI imaging" it is meant substantially no distortion of the imaged area by MRI artifact such as "blooming" due to metallic pieces or components, and substantially no local distortion of the magnetic field caused by a mass material, such that the tissue receiving port 136 can be identified using MRI imaging.

The proximal needle segment 140 is disposed proximally of the tissue receiving port 136, and extends proximally of the distal needle segment 160. The proximal needle segment 140 is formed at least in part of a second material different from the first material.

A distal tissue piercing tip 190 can be disposed at the distal end of the needle assembly 120, such as by attachment to the distal end of the distal needle segment 160. The distal tissue piercing tip 190 is disposed distal of the tissue receiving port 136. The distal tissue piercing tip 190 can be formed of a material that does not interfere with MRI imaging of the tissue receiving port 136. In one embodiment, the piercing tip 190 can be formed of a material different from the first material and the second material. For instance, piercing tip 190 can comprise a flat blade formed of a suitable material such as a glass or ceramic.

The distal needle segment can be formed of a first material which is non-metallic and non-magnetic. In one embodiment, the first material can be selected from materials including, but limited to, plastics, thermoplastics, thermoresins, and polymers. For instance, the distal needle segment can be formed, at least in part, of a liquid crystal polymer or a glass reinforced polymer. One suitable material is a glass reinforced liquid crystal polymer such as VECTRA A130 available from Ticona Corp. In one embodiment, the first material can have a melt flow index of at least about 10 grams/minute, more particularly at least about 15 grams/minute. Without being limited by theory, such a mold flow index is thought to be beneficial for molding relatively long, thin-walled cross-sections.

The proximal needle portion 140 can be formed of a second material which is a non magnetic metal. Suitable materials from which the proximal needle portion 140 can be formed include, but are not limited to, aluminum, aluminum alloys, stainless steel, titanium, titanium alloys, and combinations thereof. In one particular embodiment, the proximal needle portion 140 can be formed of titanium, and the distal needle portion 160 can be injection molded over the titanium proximal needle portion 140, as described more fully below. The piercing tip 190 can be formed of a material selected from ceramics and glasses. In one embodiment, the tip 190 can be formed, at least in part, of a ceramic comprising alumina or zirconia. The piercing tip 190 can also be formed of a natural or synthetic gemstone, such as a natural or synthetic ruby or sapphire.

Referring to the cross-sectional illustration of FIG. 9, the distal needle segment 160 can include an upper cutter lumen 162 and a lower vacuum lumen 164, with interlumen vacuum holes 123 providing flow communication between the lumen 162 and the lumen 164. The proximal needle segment 140 can include an upper cutter lumen 142 and a lower vacuum lumen 144. Cutter lumen 142 and cutter lumen 162, together, form a continuous, smooth, uninterrupted lumen for receiving a rotating and reciprocating cutter, such as the cutter 21 described above with respect to FIGS. 1-6. Vacuum lumen 144 and vacuum lumen 164, together, form a continuous, uninterrupted lumen for conveying vacuum from a vacuum source (not shown) to the interlumen vacuum holes 123.

Still referring to FIG. 9, the distal needle portion 160 can also include fluid passages 166. Fluid-passages 166 can extend from an outside surface of the distal needle portion 160, such as the bottom surface, and can communicate with the vacuum lumen 164. In FIG. 9, the fluid passages 166 are generally cylindrically shaped holes positioned generally opposite and below the vacuum holes 123, and the passages 166 extend generally downward from the lumen 164 to extend through the exterior bottom surface of the distal needle portion 160, opposite the tissue port 136. Alternatively, the holes 166 can also be positioned to extend from the vacuum lumen 164 at various circumferential positions around the distal needle portion. Without being limited by theory, the fluid holes 166 can be used to aid in providing suction and irrigation at the biopsy site. For instance, fluid holes 166 can be used to deliver an anesthetic substance, other medications, to irrigate the biopsy site, or provide suction at the opposite end of the needle from the tissue receiving port 136.

By way of example, the proximal needle portion 140 can be formed of thin wall titanium tubing, and the distal needle portion 160 can be a liquid crystal polymer molded over an end of the proximal needle portion 140, so that a proximal portion of the distal needle portion 160 overlaps the distal portion of the proximal needle portion 140. For example, the proximal needle portion 140 can be formed by welding or otherwise joining two pieces of thin walled titanium tubing, such as upper tube portion 146 and lower tube portion 148, to form the upper lumen segment 142 and lower lumen segment 144. The distal needle portion 160 can then be molded over the proximal needle portion 140. In FIG. 9, the piercing tip 190 is illustrated with an anchoring hole 192. Anchoring hole 192 can aid in attaching piercing tip 190 to the end distal needle portion 160 when the distal needle portion 160 is formed by molding (i.e. the molten molding material flows into hole 192 and when solidified, serves to fix piercing tip 190 at the distal end of the distal needle portion 160.

Still referring to FIG. 9, the distal most portion of the proximal needle portion 140 is preferably spaced a distance L of at least about 0.5 inch from the proximal edge 136B of the port 136. In particular, the distal end of tube portion 146 is spaced a distance L from the proximal edge 136B, as shown in FIG. 9. In one embodiment, the distance L can be between about 0.5 inch and about 2.5 inches, and more particularly between about 0.5 and about 1.5 inches. Without being limited by theory, providing such a spacing can reduce interference with MRI imaging of the portion of the needle surrounding the tissue receiving port 136 by the metal of proximal needle portion 140, while maintaining the strength and stiffness of the needle assembly 120.

Figure 10:
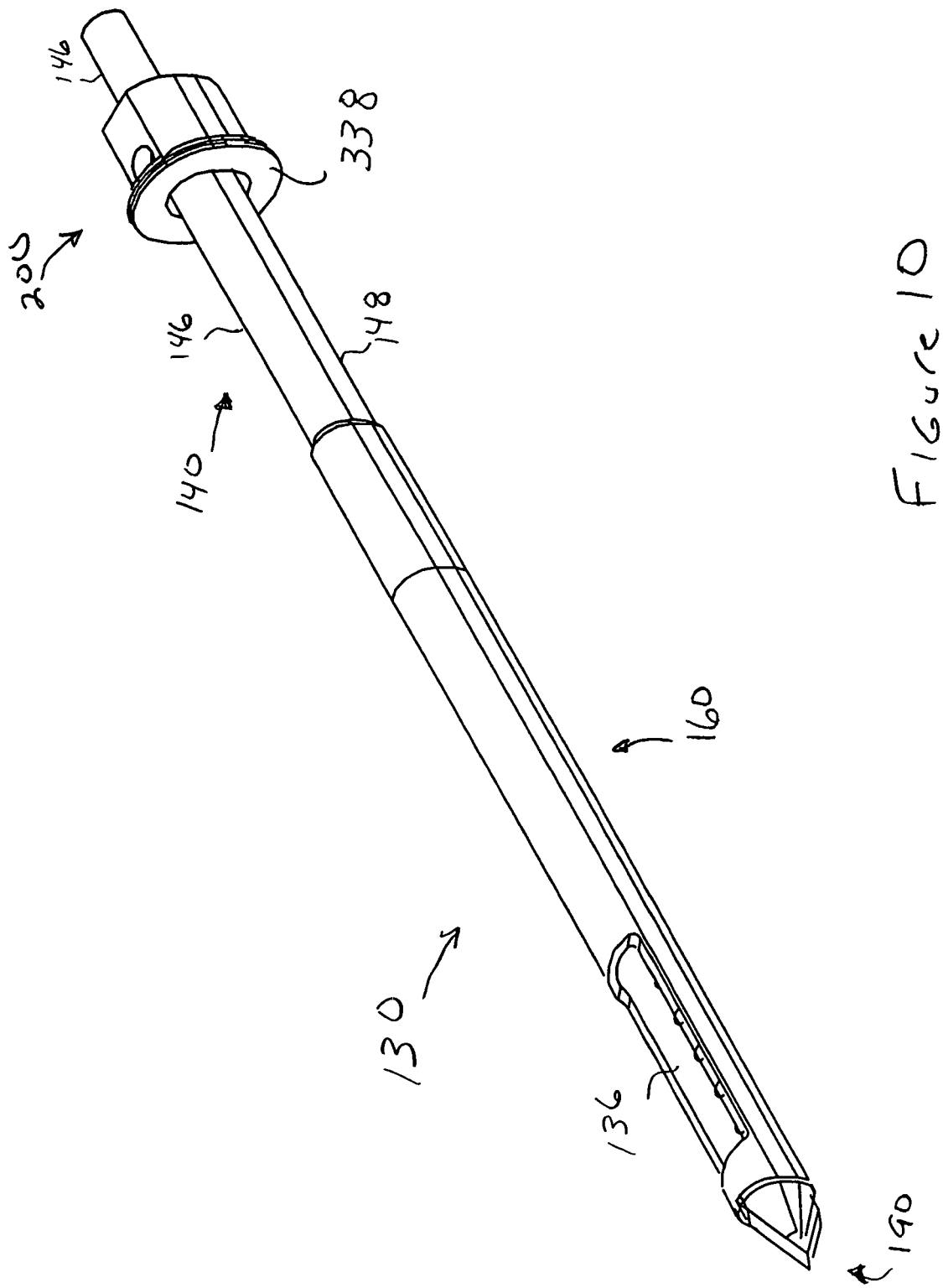
FIG. 10 is an isometric illustration of a composite needle according to an embodiment of the present invention and having a mounting flange molded to a proximal needle portion.
Figure 11:
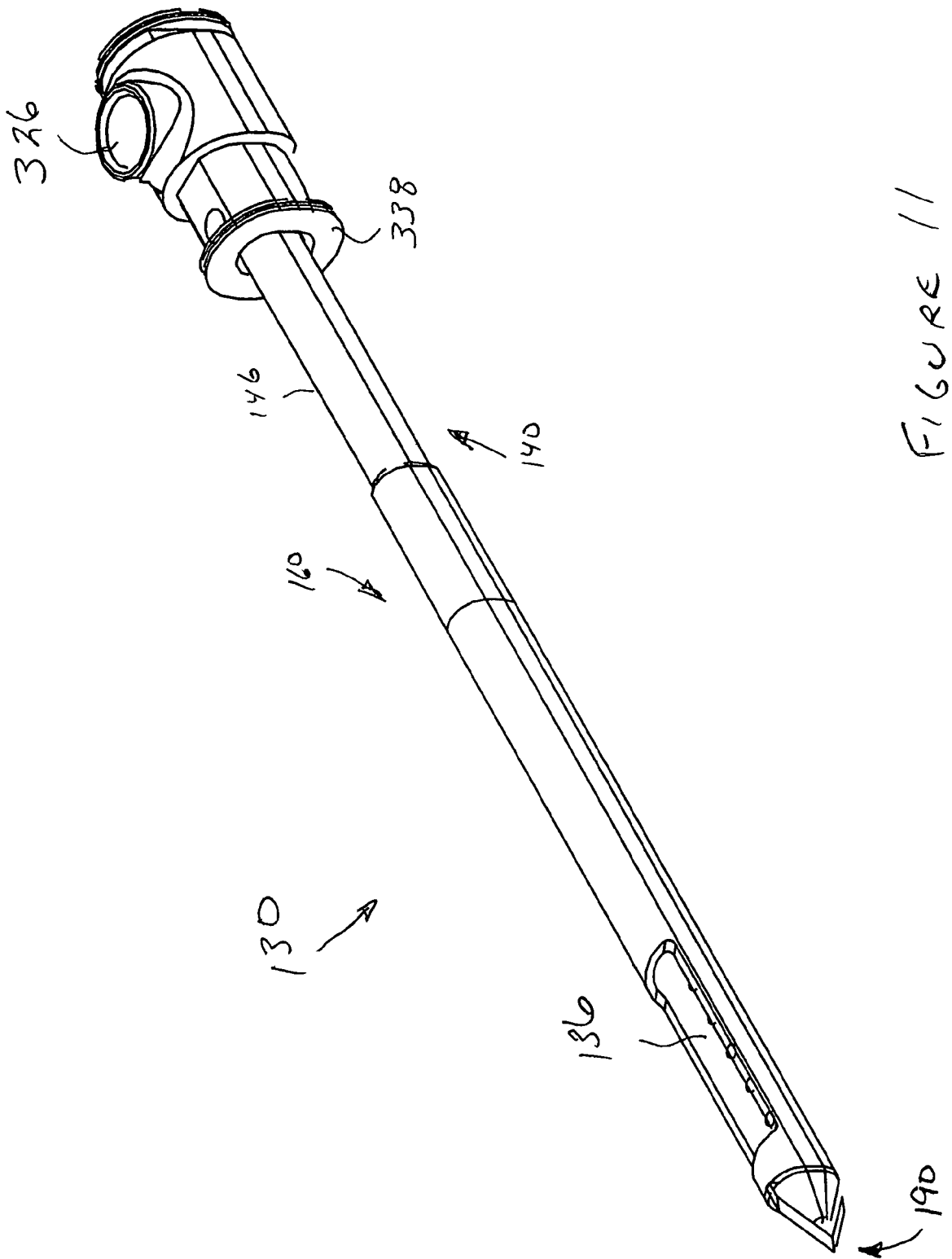
FIG. 11 is an isometric illustration of the needle of FIG. 10 with a vacuum manifold component attached to the mounting flange.

FIG. 10 illustrates needle 130 having a component 200 comprising a mounting flange 338 attached adjacent a proximal end of the needle 130. Component 200 with flange 338 can be molded onto the proximal needle portion 140, either before or after the distal needle portion 160 is molded onto the proximal needle portion 140. In one embodiment, the flange 338 can be molded onto a metallic proximal needle portion 140 first, and the distal facing surface of flange 338 can be used as a reference surface/locating surface in a subsequent molding operation in which the distal needle portion 160 is molded onto the proximal needle portion. FIG. 11 shows a vacuum manifold 326 attached to the mounting flange 338, such as by gluing, welding, or press fit. The needle, as shown in FIG. 11, can be used in the device of FIG. 1, as a replacement needle for the needle assembly shown in FIG. 2.

Figure 12:
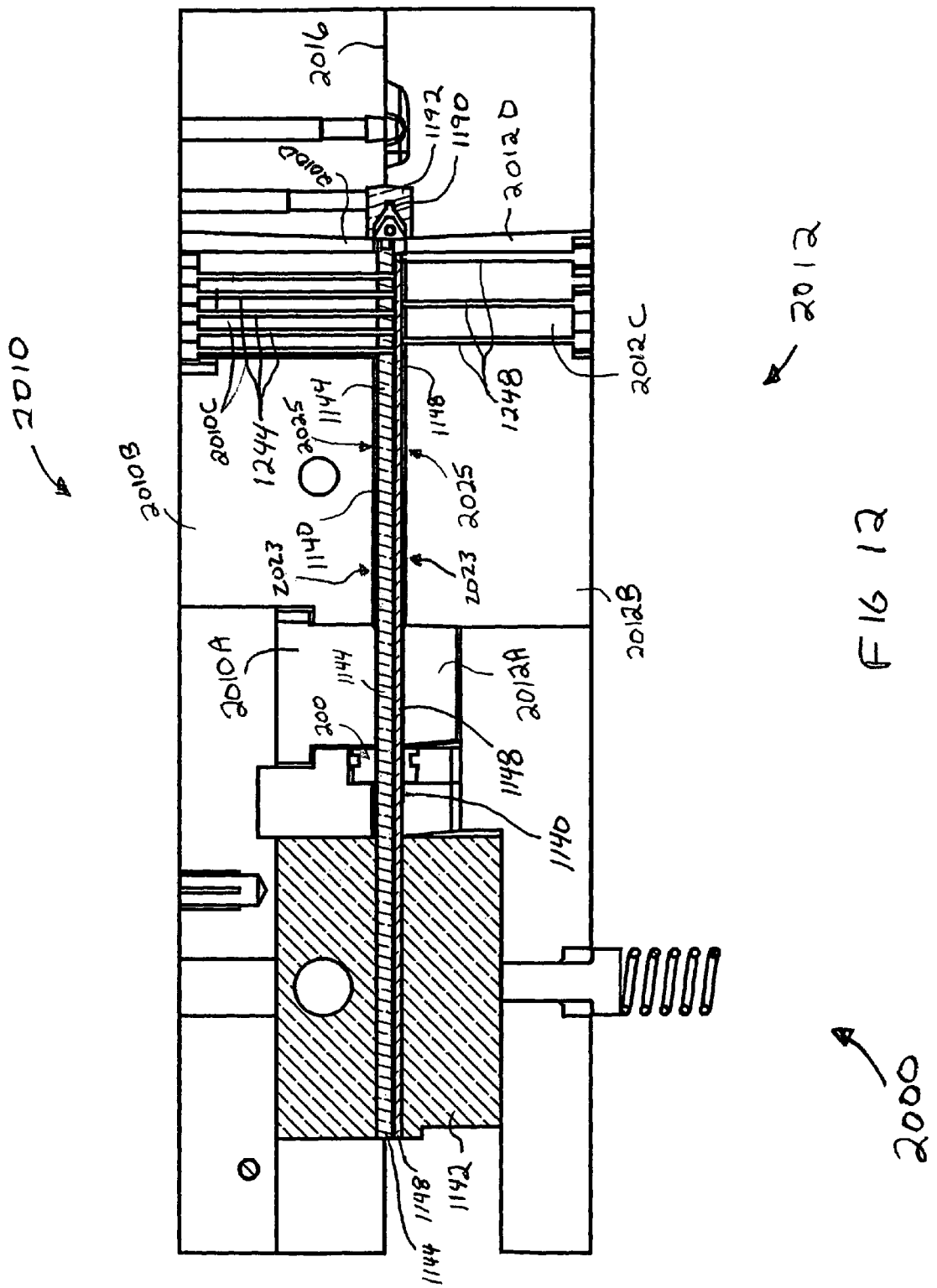
FIG. 12 is a schematic cross-sectional illustration of a mold assembly which can be used to form a biopsy device according to the present invention.

FIG. 12 illustrates a mold configuration that can be used to form a needle assembly 130. As described above, a mounting component 200 can be first molded onto a metallic proximal needle component, such as a metallic needle shaft 1140. A surface of the mounting component 200 can then serve to locate other features to molded in the distal needle portion 160.

Referring to FIG. 12, a mold assembly 2000 comprising a first mold half 2010 and a second mold half 2012 is provided. Mold halves 2010 and 2012 separate along mold split line 2016. A metallic needle shaft 1140 (corresponding to proximal needle portion 140) with a mounting component 200 molded thereto is provided. The needle shaft 1140 can include an upper lumen and a lower lumen corresponding to a portion of the cutter lumen and the vacuum lumen in the completed biopsy device. The previously molded component 200 has one or more surfaces that can be used to locate features to be molded in the mold assembly 2000.

The shaft 1140 is supported by core support shafts 1144 and 1148. Core support shafts 1144 and 1148 are supported by and extend from a support block 1142. Core support shaft 1144 extends distally from support block 1142 and extends into and through the upper lumen of needle shaft 1140. Core support shaft 1148 extends distally from support block 1142 and extends into and through the lower lumen of needle shaft 1140. The core support shafts 1144 and 1148 extend through the needle shaft 1140 and extend beyond the distal end of the needle shaft 1140. The core support shafts 1144 and 1148 serve to form the upper and lower lumens in the molded, non metallic distal needle portion of the needle assembly (molten mold material flows around the core support shafts to form the distal needle portion 160). The core support shafts can be formed of any suitable metallic or non-metallic material. In one embodiment, the core support shafts comprise stainless steel, though other metals may be employed.

The needle shaft 1140, support block 1142, and core support shafts 1144 and 1148 are inserted into the mold assembly 2000. A metal blade 1190 is supported in the mold assembly by a blade support 1192, such as a "puck" of a suitable material. A suitable material from which the puck can be formed is a liquid crystal polymer material, such as Vectra brand liquid crystal polymer available from Ticona Corp. The blade 1190 can be in the form of a flat metallic blade with a generally triangular shaped tip and having a hole near the base. The triangular shaped tip can be held in puck, such as by embedding the tip in the high temperature plastic material of the puck. The blade 1190 serves to form the piercing tip 190 of the finished needle 130. The hole in the blade 1190 is provided so that molten molding material can flow into the hole and surround the portion of the blade 1190 that is not embedded in the puck.

Core support pins 1244 and 1248 are provided in association with the mold halves 2010 and 2012. As the mold halves 2010 and 2012 are closed about the needle shaft 1140 and core support shafts 1144 and 1148, the core support pins 1244 and 1248 are positioned to engage with core support shafts. Core support pins 1248 engage the core shaft 1148 and help support the core shaft 1148 at its distal end. The ends of the core support pins 1248 can extend into recesses in core shaft 1148. The core support pins 1248 also take up space when molten material is provided to the mold 2000, so as to form the fluid holes 166 in the bottom surface of the vacuum lumen (holes 166 shown in FIG. 9). The core support pins 1244 extend through core support shaft 1144 and engage the top of core support shaft 1148. Each of the core support pins 1244 serve to form one of the interlumen vacuum holes 123 (shown in FIG. 9) when molten material is solidified around the core support pins 1244.

Once the mold halves 2010 and 2012 are closed, molten plastic is injected into one or more cavities formed by the mold halves. The mold halves 2010 and 2012 can comprise multiple segments for forming different portions of the needle. For instance, mold segments 2010A and 2012A contact needle shaft 1140 without providing a cavity, so that no molten material flows over the proximal end of needle shaft 1140. Mold segments 2010B and 2012B are sized and shaped to provide a cavity 2023 about the distal portion of needle shaft 1140, and a mold cavity 2025 about the portions of the core support shafts 1144 and 1148 extending from the needle shaft 1140. Molten material flowing into the cavity 2023 and the cavity 2025, on solidifying, forms the portion of the distal needle segment 160 which is positioned proximal of the tissue receiving port 136 of the finished needle 130.

Mold segment 2010C is sized and shaped to form the tissue receiving port 136 in the upper portion of the distal needle portion 160, while mold segment 2012C is sized and shaped to form the bottom portion of the distal needle portion 160 below the tissue receiving port 136. Mold segments 2010D and 2012D, together with the puck 1192, are used to form the distal most part of distal needle portion 160 that is between tissue receiving port 136 and the piercing tip 190. Molten material flowing around the blade 1190 and through the hole in the blade serves to entrap the blade 1190 in the distal end of distal needle portion 160. Accordingly, the piercing tip 190 is entrapped in the distal end of molded distal needle portion 160.

In the embodiment described, the distal needle portion 160 is formed by injection molding the distal needle portion about the proximal needle portion. The molding step is "insert molding" in the sense that the proximal needle portion forms a part of the supporting structure as part of the molding process as well as a functional part of the finished needle assembly. Alternatively, the distal needle portion can be formed separately, and then attached by any suitable means, such as by adhesive, to the proximal needle portion 140. In yet another embodiment, the distal needle portion can be formed in symmetric half portions, similar to those shown in FIGS. 3 and 4, with the half portions then fastened together and then attached by any suitable fastening means to the proximal needle portion. Without being limited by theory, it is believed that molding the distal needle portion about the proximal needle portion provide a smooth, uninterrupted transition between the portion of the cutter lumen associated with the proximal needle portion and the portion of the cutter lumen associated with the distal needle portion, so that there is a smooth lumen surface at the interface to permit smooth translation of the cutter through the entire length of the cutter lumen. Accordingly, there is no lip, seam, or other restriction at the lumen juncture that would otherwise require an additional machining or processing step for removal. Prior to placing the metallic proximal needle portion in the mold, the outer surface of the proximal needle portion 140 can be roughened or otherwise textured, such as by bead blasting or knurling, to enhance attachment of the distal needle portion to the proximal needle portion.

While preferred embodiments of the present invention have been shown and described herein, it will be obvious to those skilled in the art that such embodiments are provided by way of example only. Numerous variations, changes, and substitutions will now occur to those skilled in the art without departing from the present invention. Additionally, each component or element can be described in terms of a means for performing the component's function. Accordingly, it is intended that the invention be limited only by the spirit and scope of the appended claims.

What is claimed is:

1. A biopsy device suitable for use with a magnetic resonance imaging machine, said device comprising an elongated needle for receiving tissue therein, the needle comprising:
   (a) a housing; and
   (b) a needle assembly extending distally from the housing, the needle assembly comprising:
      (i) a distal needle segment sized and shaped to be inserted in a patient, the distal needle segment having a proximal end and comprising a lateral tissue receiving port disposed distally of the proximal end, the lateral tissue receiving port positionable within the patient, the distal needle segment formed of a nonmetallic, first material that does not interfere with MRI imaging of a portion of the distal needle segment associated with the tissue receiving port;
      (ii) a tissue piercing associated with a distal end of the distal needle segment, wherein the lateral tissue receiving port of the distal needle segment is disposed proximal of the piercing tip; and
      (iii) a proximal needle segment disposed proximally of the tissue receiving port, the proximal needle segment formed at least in part of a metallic, second material different from said first material;

wherein the proximal needle segment and the distal needle segment provide at least one substantially continuous lumen, wherein the proximal needle segment and the distal needle segment are longitudinally joined along a common axis; and wherein a portion of the proximal needle segment extends distally of the proximal end of the distal needle segment.

2. The device of claim 1 wherein a portion of the distal needle segment is molded over a portion of the proximal needle segment.

3. The device of claim 1 wherein the second material is selected from the group comprising aluminum, aluminum alloys, stainless steel, titanium, titanium alloys, and combinations thereof.

4. The device of claim 1 wherein the proximal needle segment and the distal needle segment provide a generally continuous cutter lumen and a generally continuous vacuum lumen, wherein the cutter lumen and the vacuum lumen extend generally side by side along at least a portion of the length of the cutter lumen.

5. The device of claim 1 wherein the distal piercing tip comprises a non-metallic material.

6. The device of claim 1 wherein the distal piercing tip comprises a material selected from the group comprising ceramics and glasses.

7. The device of claim 1 wherein the proximal needle segment and the distal needle segment provide a continuous, smooth cutter lumen.

8. The device of claim 1 wherein the proximal needle segment and the distal needle segment provide a continuous vacuum lumen.

9. The device of claim 8 wherein the needle comprises at least passage extending from the vacuum lumen to an outer surface of the needle.

10. The device of claim 9 wherein the distal needle segment comprises a plurality of passages extending from the vacuum lumen to the outer surface of the needle.

11. A biopsy device suitable for use with a magnetic resonance imaging machine, said device comprising:
(a) a housing; and
(b) a needle assembly extending distally from the housing, the needle assembly comprising:
(i) a distal needle segment sized and shaped to be inserted in a patient and comprising a lateral tissue receiving port communicating with a distal cutter lumen portion, the lateral tissue receiving port positionable within the patient, and the distal needle segment formed of a first non-metallic material;
(ii) a piercing tip associated with a distal end of the distal needle segment, wherein the lateral tissue receiving port of the distal needle segment is disposed proximal of the piercing tip; and
(iii) a proximal needle segment formed at least in part of a metal, the proximal needle segment comprising a proximal cutter lumen portion, and wherein said metal is spaced proximally at least about 0.5 inch from a proximal edge of said tissue receiving port;
wherein the distal needle segment is coupled with the proximal needle segment, wherein the distal cutter lumen portion is longitudinally coupled with the proximal cutter lumen portion along a common axis.

12. The device of claim 11 wherein said metal is spaced between about 0.5 inch and about 2.5 inches from a proximal edge of said tissue receiving port.

13. The device of claim 11 wherein said metal is spaced between about 0.5 inch and about 1.5 inch from a proximal edge of said tissue receiving port.

14. A biopsy device suitable for use with a magnetic resonance imaging machine, said device comprising an elongated needle for receiving tissue therethrough, the needle comprising:
(a) a housing; and
(b) a needle assembly extending distally from the housing, the needle assembly comprising:
(i) a distal needle segment formed of a non-metallic material and having a lateral tissue receiving port communicating with a distal cutter lumen segment; wherein the distal needle segment has a proximal end:
(ii) a metallic proximal needle segment coupled with the distal needle segment and disposed proximally of the tissue receiving port, wherein the metallic proximal needle segment provides a proximal cutter lumen segment communicating with the distal cutter lumen segment, wherein the proximal needle segment has a distal end and a proximal end; and
(iii) a mounting component coupled to the metallic proximal needle segment and located substantially near the proximal end of the metallic proximal needle segment, wherein the mounting component couples the needle assembly to the housing;
wherein the distal end of the proximal needle segment is positioned distally of the proximal end of the distal needle segment.

15. The biopsy device of claim 14 wherein a portion of the distal needle segment is molded over a portion of the proximal needle segment.

16. A biopsy device suitable for use with a magnetic resonance imaging machine, the device comprising:
a handpiece;
an outer needle extending from the handpiece, the needle comprising a proximal needle segment extending outwardly from the handpiece, and a distal needle segment supported by the proximal needle segment and spaced from the handpiece by the proximal needle segment, the distal needle segment comprising a lateral tissue receiving opening;
an inner cutter having a distal end adapted to translate within the outer needle to sever tissue received in the lateral tissue receiving opening;
a tissue piercing tip associated with a distal end of the distal needle segment;
wherein the distal needle segment is formed of a non-metallic, first material suitable for use with MRI imaging of a portion of the distal needle segment associated with the tissue receiving port; and
wherein the proximal needle segment is formed at least in part of a metallic, second material different from said first material.

17. The device of claim 16 wherein the proximal needle segment and the distal needle segment provide at least one substantially continuous cutter lumen through which the distal end of the cutter translates.

18. The device of claim 17 wherein a portion of the proximal needle segment extends distally of a proximal end of the distal needle segment.

* * * * *